US00PP08363P

United States Patent [19]

Weinberger

[11] Patent Number: Plant 8,363

[45] Date of Patent: Sep. 7, 1993

[54] HYBRID PLUM TREE CV. SUPLUMTWENTY

[75] Inventor: John H. Weinberger, Fresno, Calif.

[73] Assignee: Sun World Inc., Indio, Calif.

[21] Appl. No.: 843,903

[22] Filed: Feb. 27, 1992

[51] Int. Cl.[5] ..... A01H 5/00

[52] U.S. Cl. ..... Plt./38.1

[58] Field of Search ..... Plt./38.1

*Primary Examiner*—James R. Feyrer

[57] ABSTRACT

A plum tree characterized by its large fruit, red-black color and slightly oblate shape.

1 Drawing Sheet

This invention relates to the discovery and asexual propagation of a new variety of hybrid plum tree, *Prunus salicina* cv. Suplumtwenty. The tree is an early seasoned, red-black plum cultivated for fresh fruit market. It was discovered by John H. Weinberger in an orchard of Superior Farming Co. (now Sun World, Inc.), in Madera County, Calif., and has as its seed parent Suplumeleven (U.S. Plant Pat. No. 4,902) and, as its pollen parent, Queen Rose (unpatented).

The new plum tree variety cv. Suplumtwenty may be distinguished from other presently available commercial plum cultivars by the following combination of characteristics: its larger size, its red-black color, and slightly oblate shape. The new variety holds these distinguishing characteristics through succeeding asexual propagations, as for example, by grafting.

Among the characteristics which distinguish the new variety of plum tree from its pollen parent Queen Rosa, are the following: the fruit of the Suplumtwenty variety ripens about a week later than the pollen parent. The fruit of Suplumtwenty has a much darker skin color and is much firmer than Queen Rosa.

The new variety may be distinguished from its seed parent, Suplumeleven in the following combination of characteristics: the fruit of Suplumtwenty matures about two weeks earlier than Suplumeleven and is larger in size than the seed parent. The flesh of Suplumtwenty is firmer and more yellow in appearance than that of Suplumeleven. Moreover, the lenticels of the Suplumtwenty fruit are less conspicuous. There are fewer concentric cracks on the shoulders than Suplumeleven.

The accompanying drawing illustrates, in full color, a typical stem and mature leaves of the plum tree and the ripe fruit as viewed from the stem end and in profile. The drawing also illustrates the fruit sectioned in half from end to end, one-half of the fruit shown with the stone in place in the flesh and the other half shown with the stone removed from the flesh.

Throughout this specification, color names beginning with a small letter signify that the name of that color, as used in common speech, is aptly descriptive. Color names with capital letters designate values based upon The R.H.S. Colour Chart, published by The Royal Horticultural Society, London.

The descriptive matter which follows pertains to plum trees of the new variety grafted onto Nemaguard rootstock and grown in the vicinity of Fresno, Calif. and is believed to apply to plants of the variety grown in similar conditions of soil and climate elsewhere.

TREE

When grafted on Nemaguard rootstock the tree is of medium size and medium vigor. It is upright in habit and round in shape. The foliage is of medium density. The trees are hardy, regular bearers and very productive.

The trunk is of medium thickness and in surface texture. The branches are medium in caliper and are of medium surface texture. The branches have a dull surface appearance and carry a medium number of medium-sized lenticels.

LEAVES

In general, leaves are of medium size, having an average length of about 9.8 cm. and an average width of about 4.2 cm. Leaves are elliptic in outline and upfolded in profile. Leaf blade tips curve slightly downwardly at an acute angle. The crenate leaf margin undulates slightly. The leaf apex is acuminate; the leaf base is V-shaped. Leaves are of medium thickness. Leaf color on the upper surface is about Green 137A. The upper leaf surface is smooth, with no pubescence and semi-glossy. The lower leaf surface is about Green 137D in color, weak in glossiness and no pubescence is present. The lower leaf surface is smooth in texture and has a dull surface appearance.

The petiole is of medium length and medium thickness. There are usually three medium-sized glands oppositely and alternately positioned on both the leaf base and petiole. Glands are about Green 139D in color. Stipules are persistent.

Wood (leaf) buds are medium in size and conical in shape. The position, relative to the shoot, is slightly held out, their support is of medium size and not decurrent. The time of bud burst is medium.

On flowering shoots, anthocyanin is absent. The shoots are of medium size and thickness, have a medium internode length with a medium density of buds on spurs and one year old shoots. The ratio of wood (leaf) buds to flowering buds is about ½.

FLOWERS

Flower buds are, in general, hardy, of medium size and length, pointed and freely positioned. There is some pubescence and they are about Brown 177A in color.

Flowers first bloom about February 28 and attain full bloom in medium time — on the average, around the first week of March in the vicinity of Fresno, Calif. Blooms have a duration of about 8 days. The fully opened flower is white in color, of medium size — about 2.3 cm., rosaceous in shape and the petals are free.

The peduncle is of medium length, medium thickness and pubescence is absent.

The receptacle is of medium depth. Pubescence is absent on the inner surface at white bud stage. The outer surface exhibits some pubescence.

Sepals are adpressed to petals, elliptic in shape and with some pubescence on the inner and outer surfaces.

None of the flowers has exhibited double sepals.

Petals are medium in size (about 0.9 cm.); transverse broad elliptic in shape, have medium claw length, weakly wavy margins and a medium base angle. The division of the upper margins is entire and pubescence is absent on both inner and outer surfaces and both surfaces. The petals are white in color.

The stigma is level with the anthers.

The anthers are Yellow 28A (with shadings of Red 45D) just before dehiscence.

Pollen is Yellow 12D in color.

Stamens are perigynously positioned.

Pistils are few in number, but always at least one.

Pubescence is absent in ovaries and styles.

FRUIT

The fruit, as described, was firm-ripe on June 14th. The fruit at that stage of its development is uniformly large having an axial diameter of about 5.5 cm. and a transverse diameter in the suture plane of about 6.4 cm. At right angles to the suture plane, the diameter is about 6.4 cm., thus indicating a practically uniform, symmetrical and oblate shape, but compressed transversely. The position of the maximum diameter is towards the middle. The fruit is symmetric about the suture line. Fruit ripens early (averaging mid to late June in Fresno).

The fruit is for market use and has good keeping and shipping qualities. It exhibits average resistance to insects and diseases.

The suture is an inconspicuous line — discontinuous at the apex. The ventral surface is rounded slightly, with equal lips. The depresion of the apex is distinct. The pistil base does not persist. There is no pubescence at the apex.

The stem cavity is rounded, except that it is usually elongated in the plane of the suture, with the suture showing on one side. The depth of the cavity is about 1.5 cm., and its width about 2.3 cm. No markings are present. The base of the fruit is rounded. The apex is depressed in shape. The pistil point is apical in shape.

The stem is of medium length (about 0.9 cm), glabrous and adheres with medium strength to the stone.

The skin, which is of medium thickness and of medium texture is tenacious to the flesh, displays roughness and reticulation is present. The skin is sour in taste and shows no tendency to crack. Skin color is red-black, Purple 79A to Black 202A (depending on ripeness). Down is wanting and a bloom is present. Skin is not reticulated but possesses some roughness.

The color of the flesh is surrounding the pit cavity and the pit cavity is about Greyed Yellow 160D. The amygdalin is wanting and juice is abundant. The flesh has a medium sugar content. Flesh texture is medium firm, fine and meaty. Fibers are few in number and fine and tender. Fruit ripens first at apex and produces fruit of good eating quality. The flavor is acid, mild and delicate. Aroma is wanting. The stone/flesh ratio is about 1.5/119 grams.

The stone clings, adhering to flesh over its entire surface. Fibers of the stone are short and are retained as short fiber like threads along the rides. The stone is of small size, about 2.1 cm. in length and about 1.7 cm. in breadth. The width at the stalk end of the stone is about 0.5 cm and about 1.1 cm. in thickness. The stalk end is right angled. The form of the stone in profile is generally globose. The form in ventral view is flattened. The stone's base is straight, its apex pointed and acute. The hilum is oblong. The position of the stone's maximum breadth is toward the middle and the sides and generally equal. The surface of the stone is ridged throughout. There is a partly developed outgrowing keel. The ridges are jagged. The ventral stone edge is thin and winged throughout. The dorsal stone edge is narrow with shallow, narrow grooves throughout and ridges that are continuous on either side. The color of the stone is about Greyed Yellow 161C. The stone had a slight tendency to split during the dry season.

What is claimed is:

1. A new variety of plum tree cv. Suplumtwenty as illustrated and described.

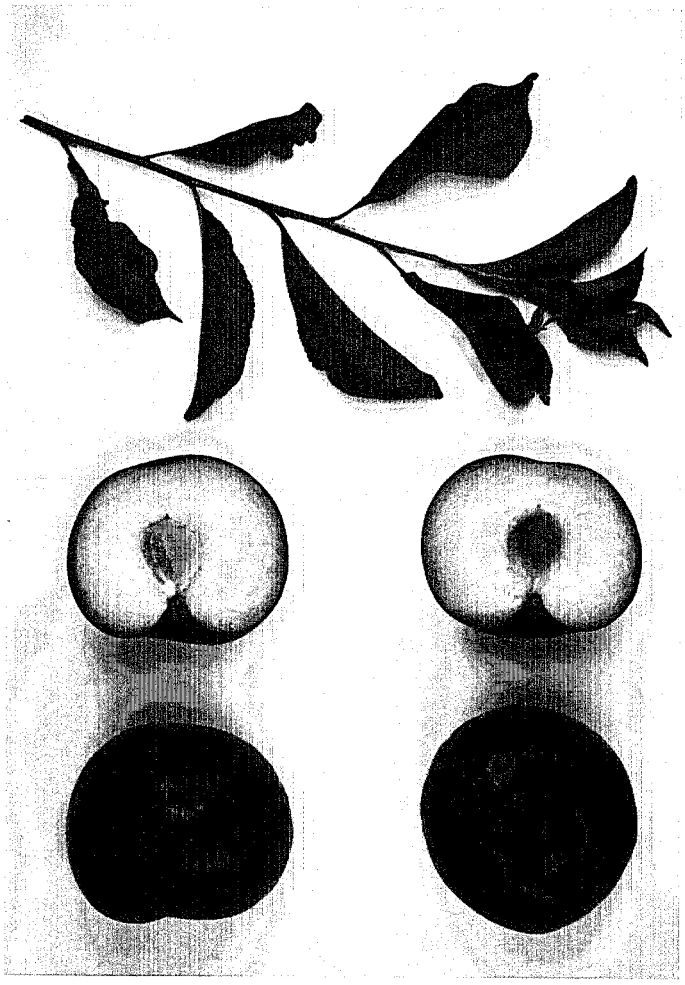

* * * * *